United States Patent
Sugiyama et al.

(10) Patent No.: US 8,778,423 B2
(45) Date of Patent: Jul. 15, 2014

(54) PROCESS FOR PRODUCTION OF PURIFIED CHLOROGENIC ACID-CONTAINING PHARMACEUTICAL PREPARATION

(75) Inventors: Yukiteru Sugiyama, Narita (JP); Kenji Yamawaki, Narita (JP); Yuko Kubo, Bunkyo-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/808,750

(22) PCT Filed: Jul. 6, 2011

(86) PCT No.: PCT/JP2011/065482
§ 371 (c)(1),
(2), (4) Date: Jan. 7, 2013

(87) PCT Pub. No.: WO2012/005293
PCT Pub. Date: Jan. 12, 2012

(65) Prior Publication Data
US 2013/0131165 A1 May 23, 2013

(30) Foreign Application Priority Data
Jul. 6, 2010 (JP) .................................. 2010-153783

(51) Int. Cl.
*A61K 36/74* (2006.01)
*A61K 36/185* (2006.01)

(52) U.S. Cl.
USPC .......................................... 424/776; 424/725

(58) Field of Classification Search
None
See application file for complete search history.

(56) References Cited

U.S. PATENT DOCUMENTS

| 2007/0248727 A1 | 10/2007 | Konishi et al. |
| 2009/0053381 A1 | 2/2009 | Fukuda et al. |
| 2009/0092736 A1 * | 4/2009 | Koyama et al. ............... 426/648 |
| 2010/0210866 A1 * | 8/2010 | Toyohara et al. ............... 560/61 |

FOREIGN PATENT DOCUMENTS

| JP | 2003 128560 | 5/2003 |
| JP | 2004 194515 | 7/2004 |
| JP | 2006 117631 | 5/2006 |
| JP | 2006 174746 | 7/2006 |
| JP | 2006 241006 | 9/2006 |
| JP | 2008 94758 | 4/2008 |
| JP | 2008 266144 | 11/2008 |
| JP | 2011 4766 | 1/2011 |

OTHER PUBLICATIONS

International Search Report Issued Sep. 27, 2011 in PCT/JP11/65482 Filed Jul. 6, 2011.

* cited by examiner

*Primary Examiner* — Chris R Tate
(74) *Attorney, Agent, or Firm* — Oblon, Spivak, McClelland, Maier & Neustast, L.L.P.

(57) ABSTRACT

Provided is a process for producing a purified chlorogenic acid-containing preparation, which is useful for the production of a chlorogenic acid-containing beverage with reduced developability of turbidity even in an acidic range.

The process for producing a purified chlorogenic acid-containing preparation according to the present invention includes a first step of dispersing or dissolving a chlorogenic acid-containing composition as a starting material in the presence of acid clay or activated clay in a mixed solvent of an organic solvent and water, a second step of removing a deposit from a dispersion or solution obtained by the first step, a third step of adjusting a concentration of chlorogenic acids and pH in a solution, which has been obtained by the second step, to from 1.5 to 10 mass % and from 2 to 4, respectively, and a fourth step of separating the deposit formed in a concentration-adjusted solution obtained by the third step.

12 Claims, No Drawings

PROCESS FOR PRODUCTION OF PURIFIED CHLOROGENIC ACID-CONTAINING PHARMACEUTICAL PREPARATION

CROSS REFERENCE TO RELATED APPLICATION

This application is a 371 of PCT/JP2011/065482, filed on Jul. 6, 2011, and claims priority to Japanese Patent Application No. 2010-153783, filed on Jul. 6, 2010.

FIELD OF THE INVENTION

This invention relates to a process for producing a purified chlorogenic acid-containing preparation.

BACKGROUND OF THE INVENTION

As materials having bioactive functions, a variety of materials have been proposed including polyphenols as those having bioactive functions such as antioxidative effect, antihypertensive effect and hepatic function-improving effect (Patent Document 1)

Chlorogenic acids, which are one class of polyphenols, have been reported to be high in antihypertensive effect (Patent Document 2), and are expected to find a wide range of utility in supplements and diet.

Developments have hence been carried out to provide the chlorogenic acids with a higher purity and a stability. As a process for the production of a stable purified chlorogenic acid extract, for example, there has been proposed a process that adjusts a coffee extract to a specific solids concentration and then brings it into contact with acid clay and/or activated clay (Patent Document 3).

PRIOR ART DOCUMENTS

Patent Documents

Patent Document 1 JP-A-2003-128560
Patent Document 2 JP-A-2004-194515
Patent Document 3 JP-A-2008-266144

SUMMARY OF THE INVENTION

The present invention includes the following embodiments:
[1] A process for producing a purified chlorogenic acid-containing preparation, comprising:
  a first step of dispersing or dissolving a chlorogenic acid-containing composition as a starting material in the presence of acid clay or activated clay in a mixed solvent of an organic solvent and water,
  a second step of removing a deposit from a dispersion or solution obtained by the first step,
  a third step of adjusting a concentration of chlorogenic acids and pH in a solution, which has been obtained by the second step, to from 1.5 to 10 mass % and from 2 to 4, respectively, and
  a fourth step of separating the deposit formed in a concentration-adjusted solution obtained by the third step.
[2] The process as described above in [1], wherein the chlorogenic acid-containing composition as the starting material is an extract obtained from at least one kind of coffee beans selected from green coffee beans and light roast coffee beans.
[3] The process as described above in [2], wherein the light roast coffee beans have an L value of 27 or more but less than 62.
[4] The process as described above in [2], wherein the light roast coffee beans have an L value of from 27 to 60.
[5] The process as described above in [2], wherein the light roast coffee beans have an L value of from 29 to 60.
[6] The process as described above in [2], wherein the light roast coffee beans have an L value of from 29 to 55.
[7] The process as described above in any one of [1] to [6], wherein a concentration of the chlorogenic acids in the chlorogenic acid-containing composition as the starting material is from 5 to 70 mass %.
[8] The process as described above in any one of [1] to [6], wherein a concentration of the chlorogenic acids in the chlorogenic acid-containing composition as the starting material is from 10 to 60 mass %.
[9] The process as described above in any one of [1] to [6], wherein a concentration of the chlorogenic acids in the chlorogenic acid-containing composition as the starting material is from 20 to 45 mass %.
[10] The process as described above in any one of [1] to [9], wherein a content of the chlorogenic acids in solids of the chlorogenic acid-containing composition as the starting material is from 20 to 70 mass %.
[11] The process as described above in any one of [1] to [9], wherein a content of the chlorogenic acids in solids of the chlorogenic acid-containing composition as the starting material is from 25 to 60 mass %.
[12] The process as described above in any one of [1] to [9], wherein a content of the chlorogenic acids in solids of the chlorogenic acid-containing composition as the starting material is from 30 to 50 mass %.
[13] The process as described above in any one of [1] to [12], wherein the acid clay or activated clay is used in an amount of from 10 to 200 mass parts per 100 mass parts of solids in the chlorogenic acid-containing composition as the starting material.
[14] The process as described above in any one of [1] to [12], wherein the acid clay or activated clay is used in an amount of from 20 to 150 mass parts per 100 mass parts of solids in the chlorogenic acid-containing composition as the starting material.
[15] The process as described above in any one of [1] to [12], wherein the acid clay or activated clay is used in an amount of from 30 to 120 mass parts per 100 mass parts of solids in the chlorogenic acid-containing composition as the starting material.
[16] The process as described above in any one of [1] to [15], wherein the acid clay or activated clay is used in an amount of from 2.5 to 60 mass parts per 100 mass parts of the mixed solvent.
[17] The process as described above in any one of [1] to [15], wherein the acid clay or activated clay is used in an amount of from 3 to 40 mass parts per 100 mass parts of the mixed solvent.
[18] The process as described above in any one of [1] to [15], wherein the acid clay or activated clay is used in an amount of from 5 to 25 mass parts per 100 mass parts of the mixed solvent.
[19] The process as described above in any one of [1] to [18], wherein the organic solvent is ethanol.
[20] The process as described above in any one of [1] to [19], wherein a concentration of the organic solvent in the mixed solvent is from 10 to 95 mass %.

[21] The process as described above in any one of [1] to [19], wherein a concentration of the organic solvent in the mixed solvent is from 20 to 80 mass %.
[22] The process as described above in any one of [1] to [19], wherein a concentration of the organic solvent in the mixed solvent is from 30 to 70 mass %.
[23] The process as described above in any one of [1] to [19], wherein a concentration of the organic solvent in the mixed solvent is from 50 to 60 mass %.
[24] The process as described above in any one of [1] to [23], wherein the mixed solvent is used in an amount from 1 to 40 mass times relative to solids in the chlorogenic acid-containing composition as the starting material.
[25] The process as described above in any one of [1] to [23], wherein the mixed solvent is used in an amount from 2 to 30 mass times relative to solids in the chlorogenic acid-containing composition as the starting material.
[26] The process as described above in any one of [1] to [23], wherein the mixed solvent is used in an amount from 3 to 20 mass times relative to solids in the chlorogenic acid-containing composition as the starting material.
[27] The process as described above in any one of [1] to [26], further comprising, in the first step, a step of adjusting a pH of the dispersion or solution, which has been obtained by the first step, to from 4.6 to 7.
[28] The process as described above in any one of [1] to [26], further comprising, in the first step, a step of adjusting a pH of the dispersion or solution, which has been obtained by the first step, to from 4.8 to 6.8.
[29] The process as described above in any one of [1] to [26], further comprising, in the first step, a step of adjusting a pH of the dispersion or solution, which has been obtained by the first step, to from 5 to 6.6.
[30] The process as described above in any one of [1] to [26], further comprising, in the first step, a step of adjusting a pH of the dispersion or solution, which has been obtained by the first step, to from 5.2 to 6.4.
[31] The process as described above in any one of [1] to [30], further comprising, after the second step until completion of the third step, a step of adjusting a concentration of the organic solvent in the solution, which has been obtained by the second step, to 5 mass % or lower.
[32] The process as described above in any one of [1] to [30], further comprising, after the second step until completion of the third step, a step of adjusting a concentration of the organic solvent in the solution, which has been obtained by the second step, to 3 mass % or lower.
[33] The process as described above in any one of [1] to [30], further comprising, after the second step until completion of the third step, a step of adjusting a concentration of the organic solvent in the solution, which has been obtained by the second step, to 1 mass % or lower.
[34] The process as described above in any one of [1] to [33], wherein the concentration of the chlorogenic acids in the solution, which has been obtained by the second step, is from 1.5 to 10 mass %.
[35] The process as described above in any one of [1] to [33], wherein the concentration of the chlorogenic acids in the solution, which has been obtained by the second step, is from 2.5 to 9.5 mass %.
[36] The process as described above in any one of [1] to [33], wherein the concentration of the chlorogenic acids in the solution, which has been obtained by the second step, is from 3 to 9 mass %.
[37] The process as described above in any one of [1] to [33], wherein the concentration of the chlorogenic acids in the solution, which has been obtained by the second step, is from 3.5 to 8.5 mass %.
[38] The process as described above in any one of [1] to [33], wherein the concentration of the chlorogenic acids in the solution, which has been obtained by the second step, is from 4 to 8 mass %.
[39] The process as described above in any one of [1] to [38], wherein the pH of the solution obtained by the second step is adjusted to from 2.2 to 3.8.
[40] The process as described above in any one of [1] to [38], wherein the pH of the solution obtained by the second step is adjusted to from 2.5 to 3.5.
[41] The process as described above in any one of [1] to [40], wherein the pH adjustment in the third step is conducted to lower the pH by from 0.6 to 5.0 relative to the pH of the solution at a time of completion of the first step.
[42] The process as described above in any one of [1] to [40], wherein the pH adjustment in the third step is conducted to lower the pH by from 1.0 to 4.5 relative to the pH of the solution at a time of completion of the first step.
[43] The process as described above in any one of [1] to [40], wherein the pH adjustment in the third step is conducted to lower the pH by from 1.5 to 4.0 relative to the pH of the solution at a time of completion of the first step.
[44] The process as described above in any one of [1] to [40], wherein the pH adjustment in the third step is conducted to lower the pH by from 2.0 to 3.5 relative to the pH of the solution at a time of completion of the first step.
[45] The process as described above in any one of [1] to [44], wherein the pH adjustment in the third step is conducted by at least one selected from a method that adds an acid to the solution with the chlorogenic acids contained therein, a method that dissolves in an acidic aqueous solution the solution with the chlorogenic acids contained therein, and a method that brings the solution with the chlorogenic acids contained therein into contact with a cation exchange resin.
[46] The process as described above in any one of [1] to [45], wherein the pH adjustment in the third step is conducted by the method that brings the solution with the chlorogenic acids contained therein into contact with the cation exchange resin.
[47] The process as described above in [45] or [46], wherein the cation exchange resin is used in an amount of from 0.05 to 10 (mL/g) relative to a mass of the chlorogenic acid-containing composition.
[48] The process as described above in [45] or [46], wherein the cation exchange resin is used in an amount of from 0.1 to 10 (mL/g) relative to a mass of the chlorogenic acid-containing composition.
[49] The process as described above in [45] or [46], wherein the cation exchange resin is used in an amount of from 0.3 to 8 (mL/g) relative to a mass of the chlorogenic acid-containing composition.
[50] The process as described above in [45] or [46], wherein the cation exchange resin is used in an amount of from 0.5 to 4 (mL/g) relative to a mass of the chlorogenic acid-containing composition.
[51] The process as described above in [45] or [46], wherein the cation exchange resin is used in an amount of from 0.1 to 10 (mL/g) relative to a solids mass of the chlorogenic acid-containing composition.
[52] The process as described above in [45] or [46], wherein the cation exchange resin is used in an amount of from 0.2 to 5 (mL/g) relative to a solids mass of the chlorogenic acid-containing composition.

[53] The process as described above in [45] or [46], wherein the cation exchange resin is used in an amount of from 0.3 to 2 (mL/g) relative to a solids mass of the chlorogenic acid-containing composition.

[54] The process as described above in [45] or [46], wherein the cation exchange resin is used in an amount of from 0.1 to 10 (mL/g) relative to a mass of the chlorogenic acids.

[55] The process as described above in [45] or [46], wherein the cation exchange resin is used in an amount of from 0.2 to 5 (mL/g) relative to a mass of the chlorogenic acids.

[56] The process as described above in [45] or [46], wherein the cation exchange resin is used in an amount of from 0.3 to 2 (mL/g) relative to a mass of the chlorogenic acids.

[60] A purified chlorogenic acid-containing preparation, wherein an aqueous solution of the purified chlorogenic acid-containing preparation has a turbidity of 65 NTU or lower when a concentration of chlorogenic acids is adjusted to 0.6 mass and a pH is adjusted to from 2 to 4.

[61] A purified chlorogenic acid-containing preparation, wherein an aqueous solution of the purified chlorogenic acid-containing preparation has a turbidity of 65 NTU or lower when a concentration of chlorogenic acids is adjusted to 0.6 mass % and a pH is adjusted to 3.

[62] The purified chlorogenic acid-containing preparation as described above in [60] or [61], wherein the turbidity is 60 NTU or lower.

[63] The purified chlorogenic acid-containing preparation as described above in [60] or [61], wherein the turbidity is 50 NTU or lower.

[64] The purified chlorogenic acid-containing preparation as described above in [60] or [61], wherein the turbidity is 30 NTU or lower.

[65] The purified chlorogenic acid-containing preparation as described above in any one of [60] to [64], wherein a mass ratio of potassium to the chlorogenic acids [K/chlorogenic acids] is 0.18 or smaller.

[66] The purified chlorogenic acid-containing preparation as described above in any one of [60] to [64], wherein the mass ratio [K/chlorogenic acids] is from 0.001 or 0.1.

[67] The purified chlorogenic acid-containing preparation as described above in any one of [60] to [64], wherein the mass ratio [K/chlorogenic acids] is from 0.001 or 0.08.

[68] The purified chlorogenic acid-containing preparation as described above in any one of [60] to [64], wherein the mass ratio [K/chlorogenic acids] is from 0.001 or 0.06.

[69] The purified chlorogenic acid-containing preparation as described above in any one of [60] to [64], wherein the mass ratio [K/chlorogenic acids] is from 0.001 or 0.04.

[70] The purified chlorogenic acid-containing preparation as described above in any one of [60] to [69], wherein a mass ratio of a sum of potassium and sodium to the chlorogenic acids [(K+Na)/chlorogenic acids] is 0.18 or smaller.

[71] The purified chlorogenic acid-containing preparation as described above in any one of [60] to [69], wherein the mass ratio [(K+Na)/chlorogenic acids] is from 0.001 to 0.14.

[72] The purified chlorogenic acid-containing preparation as described above in any one of [60] to [69], wherein the mass ratio [(K+Na)/chlorogenic acids] is from 0.001 to 0.1.

[73] The purified chlorogenic acid-containing preparation as described above in any one of [60] to [69], wherein the mass ratio [(K+Na)/chlorogenic acids] is from 0.001 to 0.06.

[74] The purified chlorogenic acid-containing preparation as described above in any one of [60] to [73], wherein a concentration of the chlorogenic acids is 11 mass % or higher.

[75] The purified chlorogenic acid-containing preparation as described above in any one of [60] to [73], wherein a concentration of the chlorogenic acids is from 13 to 30 mass %.

[76] The purified chlorogenic acid-containing preparation as described above in any one of [60] to [73], wherein a concentration of the chlorogenic acids is from 15 to 26 mass %.

[77] The purified chlorogenic acid-containing preparation as described above in any one of [60] to [76], wherein a content of the chlorogenic acids in solids is from 10 to 80 mass %.

[78] The purified chlorogenic acid-containing preparation as described above in any one of [60] to [76], wherein a content of the chlorogenic acids in solids is from 20 to 70 mass %.

[79] The purified chlorogenic acid-containing preparation as described above in any one of [60] to [76], wherein a content of the chlorogenic acids in solids is from 30 to 60 mass %.

[80] The purified chlorogenic acid-containing preparation as described above in any one of [60] to [79], wherein a mass ratio of caffeine to the chlorogenic acids (caffeine/chlorogenic acids) is 0.05 or smaller.

[81] The purified chlorogenic acid-containing preparation as described above in any one of [60] to [79], wherein a mass ratio of caffeine to the chlorogenic acids (caffeine/chlorogenic acids) is 0.03 or smaller.

[82] The purified chlorogenic acid-containing preparation as described above in any one of [60] to [79], wherein a mass ratio of caffeine to the chlorogenic acids (caffeine/chlorogenic acids) is 0.02 or smaller.

[91] A chlorogenic acid-containing beverage, comprising the following ingredients (A) and (B):
(A) from 0.05 to 0.9 mass % of chlorogenic acids, and
(B) potassium,
wherein a mass ratio of the potassium (B) to the chlorogenic acids (A) [K/chlorogenic acids] is 0.18 or smaller, and a pH is from 1.5 to 4.

[92] The chlorogenic acid-containing beverage as described above in [91], wherein a content of the chlorogenic acids (A) is from 0.05 to 0.7 mass %.

[93] The chlorogenic acid-containing beverage as described above in [91], wherein a content of the chlorogenic acids (A) is from 0.05 to 0.6 mass %.

[94] The chlorogenic acid-containing beverage as described above in any one of [91] to [93], wherein the mass ratio [K/chlorogenic acids] is from 0.001 to 0.1.

[95] The chlorogenic acid-containing beverage as described above in any one of [91] to [93], wherein the mass ratio [K/chlorogenic acids] is from 0.001 to 0.08.

[96] The chlorogenic acid-containing beverage as described above in any one of [91] to [93], wherein the mass ratio [K/chlorogenic acids] is from 0.001 to 0.06.

[97] The chlorogenic acid-containing beverage as described above in any one of [91] to [93], wherein the mass ratio [K/chlorogenic acids] is from 0.001 to 0.04.

[98] The chlorogenic acid-containing beverage as described above in any one of [91] to [97], wherein the pH is from 1.5 to 3.5.

[99] The chlorogenic acid-containing beverage as described above in any one of [91] to [97], wherein the pH is from 2 to 3.5.

[100] The chlorogenic acid-containing beverage as described above in any one of [91] to [99], further comprising (C) sodium, wherein a mass ratio of a sum of the potassium (B) and sodium (C) to the chlorogenic acids (A) [(K+Na)/chlorogenic acids] is 0.18 or smaller.
[101] The chlorogenic acid-containing beverage as described above in any one of [91] to [99], wherein the mass ratio [(K+Na)/chlorogenic acids] is from 0.001 to 0.14.
[102] The chlorogenic acid-containing beverage as described above in any one of [91] to [99], wherein the mass ratio [(K+Na)/chlorogenic acids] is from 0.001 to 0.1.
[103] The chlorogenic acid-containing beverage as described above in any one of [91] to [99], wherein the mass ratio [(K+Na)/chlorogenic acids] is from 0.001 to 0.06.
[104] The chlorogenic acid-containing beverage as described above in any one of [91] to [103], wherein a content of the potassium in the beverage is 0.06 mass % or lower.
[105] The chlorogenic acid-containing beverage as described above in any one of [91] to [103], wherein a content of the potassium in the beverage is from 0.00001 to 0.03 mass %.
[106] The chlorogenic acid-containing beverage as described above in any one of [91] to [103], wherein a content of the potassium in the beverage is from 0.00001 to 0.02 mass %.
[107] The chlorogenic acid-containing beverage as described above in any one of [91] to [106], wherein the chlorogenic acids (A) have been derived from a green coffee bean extract.

DESCRIPTION OF THE INVENTION

With a view to finding utility of chlorogenic acids in broader applications, the present inventors conducted research on beverages with varying chlorogenic acid concentrations in a wide pH range by using chlorogenic acid-containing compositions. As a result, it was found that a chlorogenic acid-containing beverage may develop a turbidity in an acidic range when diluted to a concentration suited as a beverage.

According to the present invention, there are hence provided a chlorogenic acid-containing beverage with a reduced developability of turbidity even in the acidic range, especially a purified chlorogenic acid-containing preparation useful for the production of a chlorogenic acid-containing acidic beverage, and its production process, and also a chlorogenic acid-containing beverage making use of the preparation.

As a result of research in various ways, the present inventors found that a purified chlorogenic acid-containing preparation with a reduced developability of turbidity even in the acidic range can be obtained by bringing a chlorogenic acid-containing composition, in a form dispersed or dissolved in a mixed solvent of an organic solvent and water, into contact with a specific adsorbent, removing a deposit, controlling the concentration of the chlorogenic acids and the pH to specific ranges to form the deposit further, and conducting solid-liquid separation.

The present invention can provide a purified chlorogenic acid-containing preparation useful for the production of a chlorogenic acid-containing beverage, which is high in clarity and is also excellent in coarseness even when formulated into an acidic beverage by diluting the concentration of the chlorogenic acids to a concentration optimal to the beverage, and its production process.

Therefore, the purified chlorogenic acid-containing preparation according to the present invention is particularly useful as a starting material for an acidic beverage containing a chlorogenic acid, especially for an acidic beverage containing the chlorogenic acids.

A description will hereinafter be made about the process of the present invention for the production of a purified chlorogenic acid-containing preparation.

The process of the present invention for the production of the purified chlorogenic acid-containing preparation is characterized by including a first step, a second step, a third step, and a fourth step. Each of these steps will hereinafter be described in detail.

(First Step)

The first step according to the present invention is a step, in which a chlorogenic acid-containing composition as a starting material is dispersed or dissolved in the presence of acid clay or activated clay in a mixed solvent (hereinafter called "an aqueous organic solvent solution") of an organic solvent and water.

No particular limitation is imposed on the chlorogenic acid-containing composition as the starting material insofar as the chlorogenic acids are contained, and a plant extract containing the chlorogenic acids may be used. Examples of such a plant extract include those extracted from sunflower seeds, unripe apples, coffee beans, simon leaves, pinaceous cones, pinaceous seed hulls, sugarcane nandina leaves, burdock, eggplant skins, ume fruit, colts foot, vitaceous plants or the like. No particular limitation is imposed on the extraction method or extraction conditions, and a known method and known conditions may be adopted.

Among these, as the chlorogenic acid-containing composition as the starting material, an extract from coffee beans is preferred from the standpoint of the content of the chlorogenic acids or the like. The coffee beans to be used for extraction may preferably be green coffee beans or light roast coffee beans from the standpoint of the content of the chlorogenic acids or the like. These green coffee beans and light roast coffee beans may be used in combination. The L value of light roast coffee beans may be preferably 27 or greater, more preferably 29 or greater, from the standpoint of the content of the chlorogenic acids. The upper limit of the L value, on the other hand, may be preferably smaller than 62, more preferably 60 or smaller, even more preferably 55 or smaller from the standpoint of taste and flavor. The term "L value" as used herein means a value as determined by measuring the lightness of roasted coffee beans with a color difference meter under the assumption that black has an L value of 0 and white has an L value of 100.

The species of coffee tree may be any one of *Arabica, Robusta, Liberica* and *Arabusta*. No particular limitation is imposed on the extraction method or extraction conditions. For example, the method described in JP-A-58-138347, JP-A-59-51763, JP-A-62-111671, JP-A-5-236918 or the like may be adopted.

As the chlorogenic acid-containing composition as the starting material, a commercially-available preparation containing the chlorogenic acids may be used, and Illustrative thereof is "FLAVOR HOLDER RC" (product of T. Hasegawa Co., Ltd.)

It is to be noted that the chlorogenic acid-containing composition as the starting material may be in various forms such as, for example, a liquid, slurry, semi-solid, solid.

It is to be noted that the term "chlorogenic acids" as used herein is a generic term that collectively encompasses monocaffeoylquinic acids including 3-caffeoylquinic acid, 4-caffeoylquinic acid and 5-caffeoylquinic acid, monoferuloylquinic acids including 3-feruloylquinic acid, 4-feruloylquinic acid and 5-feruloylquinic acid, and dicaffeoylquinic acids including 3,4-dicaffeoylquinic acid, 3,5-dicaffeoylquinic acid and 4,5-dicaffeoylquinic acid. The content of the chlorogenic acids is defined based on the total amount of the above-described nine chlorogenic acids.

The concentration of the chlorogenic acids in the chlorogenic acid-containing composition as the starting material may be preferably from 5 to 70 mass %, more preferably from 10 to 60 mass %, even more preferably from 20 to 45 mass % from the standpoints of work efficiency and solubility.

Also, the content of the chlorogenic acids in the solids of the chlorogenic acid-containing composition as the starting material may be preferably from 20 to 70 mass %, more preferably from 25 to 60 mass %, even more preferably from 30 to 50 mass %. It is to be noted that the term "solids" as used herein means the residue remaining after volatiles have been removed by drying a sample for 3 hours in an electric constant-temperature drier controlled at 105° C.

No particular limitation is imposed on acid clay or activated clay insofar as both of them contain, as general chemical components, $SiO_2$, $Al_2O_3$, $Fe_2O_3$, CaO, MgO or the like, and those having an $SiO_2/Al_2O_3$ mass ratio of from 3 to 12, preferably from 4 to 9 are preferred. Also preferred are those which have a composition containing from 2 to 5 mass % of $Fe_2O_3$, from 0 to 1.5 mass % of CaO and from 1 to 7 mass % of MgO.

Activated clay is obtained by treating a naturally-mined acid clay (montmorillonite clay) with a mineral acid such as sulfuric acid, and is a compound having a porous structure of large specific surface area and adsorptive capacity. Further treatment of acid clay with an acid makes it possible to change its specific surface area such that its decoloring ability is improved and its physical properties are modified.

The specific surface areas of acid clay and activated clay may preferably be from 50 to 350 $m^2/g$, depending on the degree of the acid treatment or the like, and their pH (5% suspensions, 20° C.) may be preferably from 2.5 to 8, more preferably from 3.6 to 7. As acid clay, for example, a commercially-available product such as "MIZUKA ACE #600" (product of Mizusawa Chemical Industries, Ltd.) may be used.

Of acid clay and activated clay, acid clay is suitably used in this step.

Acid clay or activated clay is used, from the viewpoint of a reduction in turbidity, in an amount of preferably from 10 to 200 mass parts, more preferably from 20 to 150 mass parts, even more preferably from 30 to 120 mass parts per 100 mass parts of the solids in the chlorogenic acid-containing composition as the starting material.

Acid clay or activated clay is used, from the viewpoints of stirring efficiency and dispersion efficiency, in an amount of preferably from 2.5 to 60 mass parts, more preferably from 3 to 40 mass parts, even more preferably from 5 to 25 mass parts per 100 mass parts of the aqueous organic solvent solution.

The organic solvent is, for example, an alcohol such as ethanol or methanol, a ketone such as acetone, or an ester such as ethyl acetate. Among these, a hydrophilic organic solvent such as an alcohol and a ketone is preferred. In view of use in foods, the alcohol is more preferred, with ethanol being more preferred.

The concentration of the organic solvent in the aqueous organic solvent solution may be, from the viewpoints of a reduction in turbidity and improvements in taste and flavor, preferably from 10 to 95 mass %, more preferably from 20 to 80 mass %, more preferably from 30 to 70 mass %, even more preferably from 50 to 60 mass %.

No particular limitation is imposed on a method for adjusting the concentration of the aqueous organic solvent solution. Illustrative are, for example, to mix the organic solvent and water such that the concentration of the organic solvent falls within the above-described range; to dissolve the chlorogenic acid-containing composition as the starting material in water and then to add the organic solvent thereto such that the concentration of the organic solvent is adjusted to the above-described range; and to suspend the chlorogenic acid-containing composition as the starting material in the organic solvent and then to gradually add water thereto such that the concentration of the organic solvent is adjusted to the above-described range.

The aqueous organic solvent solution is used, from the viewpoints of a reduction in turbidity and improvements in taste and flavor, in an amount preferably from 1 to 40 mass times, more preferably from 2 to 30 mass times, even more preferably from 3 to 20 mass times relative to the solids in the chlorogenic acid-containing composition as the starting material.

In this step, upon mixing the chlorogenic acid-containing composition as the starting material with the aqueous organic solvent solution, acid clay or activated clay may be added to prepare a dispersion or mixed solution. Alternatively, all of them may be added at the same time to prepare a dispersion or mixed solution.

The pH (20° C.) of the dispersion or solution obtained by mixing the chlorogenic acid-containing composition as the starting material with the aqueous organic solvent solution may be, from the viewpoints of a reduction in turbidity and improvements in taste and flavor, preferably from weakly acidic to neutral, more specifically in a range of preferably from 4.6 to 7, more preferably from 4.8 to 6.8, more preferably from 5 to 6.6, even more preferably from 5.2 to 6.4.

(Second Step)

The second step according to the present invention is a step, in which a deposit in the dispersion or solution obtained by the first step is removed. This removal can effectively reduce a development of turbidity in a purified chlorogenic acid-containing preparation to be obtained finally.

As a method for removing the deposit, any method commonly used in the food industry may be applied. Examples include solid-liquid separation methods such as paper filtration, centrifugal separation, membrane filtration, and diatomaceous earth filtration. Two or more of these methods may be conducted in combination.

As a centrifuge for use in centrifugal separation, conventional equipment such as a separation-plate-type centrifuge, cylinder-type centrifuge or decanter-type centrifuge may be used. As conditions for centrifugal separation, the temperature is preferably from 5 to 70° C., more preferably from 10 to 40° C. from the viewpoint of the removal of turbid components. The rotational speed and time may be set preferably at from 2,000 to 10,000 r/min, more preferably at from 2,500 to 9,000 r/min, even more preferably at from 3,000 to 8,000 r/min for from 0.2 to 75 minutes, more preferably for from 0.5 to 60 minutes, even more preferably for from 1 to 30 minutes.

As treatment conditions for membrane filtration, the treatment may be conducted under general filtration conditions from the viewpoint of the removal of turbid components, and the membrane pore size may be preferably from 0.1 to 10 μm, more preferably from 0.2 to 5 μm, even more preferably from 0.25 to 2 μm from the viewpoints of the efficiency of filtration and the removal of turbid components. As a measuring method of the membrane pore size, a general measuring method making use of the mercury intrusion porosimetry, bubble point test, bacterial filtration porosimetry or the like may be exemplified. It is preferred to use a value determined by the bubble point test. As the material of membranes for use in membrane filtration, polymer membranes, ceramic membranes, stainless steel membranes or the like may be exemplified.

As a treatment method by diatomaceous earth filtration, the treatment may be conducted, from the viewpoint of the removal of turbid components, with a general filter aid composed of cellulose, diatomaceous earth or a combination thereof under a general filter conditions.

(Third Step)

The third step according to the present invention is a step, in which the concentration and pH of the chlorogenic acids in the solution obtained by the second step are adjusted to from 1.5 to 10 mass % and from 2 to 4, respectively. By this step, a concentration-adjusted solution is obtained. By adjusting to such a concentration of the chlorogenic acids and such a pH, a deposit is allowed to occur in the concentration-adjusted solution.

In this step, the concentration of the chlorogenic acids in the solution, which has been obtained by the second step and contains the chlorogenic acids, is adjusted to from 1.5 to 10 mass %. From the viewpoints of a reduction in turbidity, taste and flavor, the concentration may be adjusted to preferably from 2.5 to 9.5 mass %, more preferably from 3 to 9 mass %, more preferably from 3.5 to 8.5 mass %, even more preferably from 4 to 8 mass %.

As a method for adjusting the concentration of the chlorogenic acids, the concentration may be adjusted to the above-described range, for example, by dilution with added water.

In this step, the pH (20° C.) of the solution containing the chlorogenic acids is also adjusted to from 2 to 4. From the viewpoints of a reduction in turbidity, taste and flavor, a range from strongly acidic to weakly acidic is preferred. The pH may be adjusted preferably from 2.2 to 3.8, more preferably from 2.5 to 3.5.

The pH in this step may be adjusted such that it is lowered by a range of preferably from 0.6 to 5.0, more preferably from 1.0 to 4.5, more preferably from 1.5 to 4.0, even more preferably from 2.0 to 3.5 relative to the pH at a time of completion of the first step.

As a pH adjustment method, there is mentioned a method that adds an acid to the solution with the chlorogenic acids contained therein, a method that dissolves in an acidic aqueous solution the solution with the chlorogenic acids contained therein, or a method that brings the solution with the chlorogenic acids contained therein into contact with a cation exchange resin or the like. These methods may be conducted either singly or as a combination of two or more.

Examples of the acid for use in the pH adjustment include organic acids such as citric acid, lactic acid, tartaric acid, succinic acid, malic acid or ascorbic acid, and inorganic acids such as phosphoric acid or hydrochloric acid. It is to be noted that the concentration of an acid in the acidic aqueous solution may be suitably chosen to give a desired pH. It is also to be noted that the acid may be adjusted to a desired concentration by using it in combination with sodium bicarbonate or the like.

Examples of the cation exchange resin include cation exchange resins having sulfonic acid groups, carboxyl groups, phosphoric acid groups or the like. Among these, cation exchange resins having sulfonic acid groups are preferred. Specifically, "AMBERLITE 200CT, IR120B, IR124 and IR118" (products of Organo Corporation, suppler: Rohm & Haas USA), "DIAION SK1B, SK1BH, SK102, PK208 and PK212" (products of Mitsubishi Chemical Corporation) or the like may be used.

Of such pH adjustment methods, preferred is to bring the solution into contact with a cation exchange resin in H-type. The cation exchange resin is used, from the viewpoints of improvements in taste and flavor and purification efficiency, in an amount of preferably from 0.05 to 10 (mL/g), more preferably from 0.1 to 10 (mL/g), more preferably from 0.3 to 8 (mL/g), even more preferably from 0.5 to 4 (mL/g) relative to the mass of the chlorogenic acid-containing composition, in an amount of preferably from 0.1 to 10 (mL/g), more preferably from 0.2 to 5 (mL/g), even more preferably from 0.3 to 2 (mL/g) relative to the mass of the solids in the chlorogenic acid-containing composition, or in an amount of preferably from 0.1 to 10 (mL/g), more preferably from 0.2 to 5 (mL/g), even more preferably from 0.3 to 2 (mL/g) relative to the mass of the chlorogenic acids in the chlorogenic acid-containing composition.

As a method for bringing the solution into contact with the cation exchange resin, a batch method, a continuous method or the like is mentioned. Of these, preferred, from the viewpoint of purification efficiency, is the continuous method that packs the cation exchange resin in a column and the solution is continuously passed therethrough. In the case of the continuous method, the superficial velocity of the solution to be passed may be preferably from 1 to 30 $h^{-1}$, more preferably from 1.5 to 20 $h^{-1}$, even more preferably from 2 to 15 $h^{-1}$.

Upon bringing the chlorogenic acid-containing composition into contact with the cation exchange resin, the chlorogenic acid-containing composition may be preferably included in water or an aqueous organic solvent solution, with the one being preferably included in the aqueous organic solvent solution from the viewpoints of improvements in taste and flavor and purification efficiency.

The organic solvent includes, for example, an alcohol such as ethanol or methanol, a ketone such as acetone, or an ester such as ethyl acetate. Among these, hydrophilic organic solvents such as alcohols and ketones are preferred. In view of use in foods, alcohols are more preferred, with ethanol being even more preferred.

In this step, the solution with the chlorogenic acids contained therein may be treated further with activated carbon.

The treatment with activated carbon may be conducted either separately from or concurrently with the pH adjustment. It is preferred to conduct the contact with the ion exchange resin after the treatment with activated carbon.

The treatment with activated carbon may be conducted by either a batch method or a continuous method. For example, the activated carbon and the cation exchange resin are packed in separate columns, and the treatment with the activated carbon may be conducted by a continuous method; or the activated carbon and the cation exchange resin are packed in the same column, and the treatment with the activated carbon may be conducted by a continuous method.

No particular limitation is imposed on the activated carbon to be used in the present invention insofar as it is commonly used for industrial applications. Usable examples include commercially-available products such as "ZN-50" (product of Hokuetsu Carbon Industry Co., Ltd.), "KURARAY COAL GLC", "KURARAY COAL PK-D" and "KURARAY COAL PW-D" (products of Kuraray Chemical K.K.), and "SHIROWASHI AW50", "SHIROWASHI A", "SHIROWASHI M", "SHIROWASHI C" and "SHIROWASHI WH2C" (products of Japan EnviroChemicals, Ltd.).

The pore volume of the activated carbon is preferably from 0.05 to 1.6 mL/g, more preferably from 0.1 to 1.2 mL/g. The specific surface area is preferably from 700 to 1,800 $m^2/g$, more preferably from 900 to 1,600 $m^2/g$. It is to be noted that these physical values are those determined by the nitrogen adsorption method.

The activated carbon is used, from the viewpoints of removal of turbidity and improvements in taste and flavor, in an amount from 0 to 3.0 mass times, more preferably from 0 to 1.8 mass times, more preferably from 0 to 1.5 mass times, more preferably from 0.1 to 1.2 mass times, even more preferably from 0.2 to 1.0 mass times relative to the content of the chlorogenic acids in the chlorogenic acid-containing composition as the starting material.

The contact with the activated carbon may be conducted at preferably from 0 to 60° C., more preferably from 10 to 50° C., even more preferably from 15 to 40° C.

Filtration processing may also be conducted before the concentration or pH adjustment and after the treatment with the activated carbon. As a method for the filtration processing, any method commonly used in the food industry may be applied. Examples include solid-liquid separation methods such as paper filtration, centrifugal separation, membrane filtration or diatomaceous earth filtration. Two or more of these methods may be conducted in combination.

After the second step until completion of the third step, it may be to include a step of adjusting the concentration of the organic solvent to adjust the concentration of the organic solvent in the solution with the chlorogenic acids contained therein such that it is adjusted to preferably 5 mass % or lower, more preferably 3 mass % or lower, even more preferably 1 mass % or lower.

This step of adjusting a concentration of the organic solvent may be conducted before the pH adjustment in the third step. It may be conducted preferably after the pH adjustment with the cation exchange resin in the third step. In this case, a further pH adjustment may be conducted without any problem after the organic solvent concentration adjusting step.

Further, this solvent concentration adjusting step may be conducted without any problem either before or after the adjustment of the concentration of the chlorogenic acids in the third step. It may be conducted preferably before the adjustment of the concentration of the chlorogenic acids.

By the organic solvent concentration adjusting step, the efficiency of separation of turbid components can be increased to obtain a purified chlorogenic acid-containing preparation of still higher clarity. It is to be noted that the concentration of the organic solvent in the solution with the chlorogenic acids contained therein may be 0 mass %.

As a method for adjusting the concentration of the organic solvent, illustrative are to lower the concentration of the organic solvent by distillation under reduced pressure or normal pressure, extraction, membrane separation or the like, as well as to lower the concentration of the organic solvent by adding water thereto.

(Fourth Step)

The fourth step according to the present invention is a step, in which a deposit formed in the concentration-adjusted solution obtained by the third step is separated. By this separation, it is possible to reduce the occurrence of turbidity when formulating into a beverage.

As a method for separating the deposit, the solid-liquid separation methods mentioned above as methods for the removal of the deposit may each be adopted. Among them, centrifugal separation is preferred. By the separation, the components that cause turbidity can be removed from the chlorogenic acid-containing composition to obtain a purified chlorogenic acid-containing preparation having high clarity and also a good taste and flavor.

The purified chlorogenic acid-containing preparation according to the present invention can be obtained as described above. The purified chlorogenic acid-containing preparation may be in various forms such as, for example, liquid, slurry, semi-solid and solid.

When the product form of the purified chlorogenic acid-containing preparation is a liquid, slurry or semi-solid, the concentration of the chlorogenic acids contained in the preparation may be, from the viewpoint of distribution, preferably 1 mass % or higher, more preferably 5 mass % or higher, more preferably 10 mass % or higher, even more preferably 22 mass % or higher.

Further, the purified chlorogenic acid-containing preparation may be distributed by freezing its liquid from the viewpoint of avoiding a reduction in quality. When the liquid is frozen, the concentration of the chlorogenic acids may be preferably 11 mass % or higher, more preferably from 13 to 30 mass %, even more preferably from 15 to 26 mass % from the viewpoints of allowing to maintain the clarity of the purified chlorogenic acid-containing preparation after thawing.

As a method for adjusting to the above-described concentration of the chlorogenic acids, a concentration method is preferred. The concentration method includes the normal-pressure concentration method that conducts the evaporation of the solvent under normal pressure, the reduced-pressure concentration method that conducts the evaporation of the solvent under reduced pressure, or the membrane concentration method that removes the solvent by membrane separation or the like, with the reduced-pressure concentration method being preferred from the standpoints of work efficiency and quality improvements. The temperature during the concentration may be preferably from 20 to 70° C., more preferably from 25 to 65° C., even more preferably from 30 to 60° C.

When the purified chlorogenic acid-containing preparation is a solid as its product form, it may be powderized by a known method such as spray drying or freeze drying.

The purified chlorogenic acid-containing preparation obtained by the production process according to the present invention can have the following features (i) to (v).

(i) An aqueous solution of the purified chlorogenic acid-containing preparation may have, from the viewpoints of appearance and stability, a turbidity of preferably 65 NTU or lower, more preferably 60 NTU or lower, still more preferably 50 NTU or lower, even more preferably 30 NTU or lower when the concentration of the chlorogenic acids is adjusted to 0.6 mass % and the pH is adjusted to from 2 to 4. It is to be noted that the term "turbidity" as used herein in the above-described context means a value measured by a method to be described in Examples. It is also to be noted that the term "NTU" means the measurement unit of Formazin turbidity making use of Formazin Turbidity Standard.

(ii) The purified chlorogenic acid-containing preparation may contain, from the viewpoint of taste and flavor, the chlorogenic acids at preferably from 10 to 80 mass %, more preferably from 20 to 70 mass %, even more preferably from 30 to 60 mass % based on the solids thereof.

(iii) In the purified chlorogenic acid-containing preparation, the mass ratio of caffeine to the chlorogenic acids (caffeine/chlorogenic acids) may be, from the viewpoint of taste and flavor, preferably 0.05 or smaller, more preferably 0.03 or smaller, even more preferably 0.02 or smaller. It is to be noted that the lower limit of the mass ratio of caffeine/chlorogenic acids is not specifically limited and may be 0.

(iv) In the purified chlorogenic acid-containing preparation, the mass ratio [(K+Na)/chlorogenic acids] of the sum of potassium (K) and sodium (Na) to the chlorogenic acids may be, from the viewpoint of taste and flavor, preferably 0.18 or smaller, more preferably 0.14 or smaller, still more preferably 0.1 or smaller, even more preferably 0.06 or smaller. It is to be noted that the lower limit of the mass ratio ((K+Na)/chlorogenic acids) is not specifically limited and may be 0. From the viewpoint of production efficiency, the lower limit of the mass ratio ((K+Na)/chlorogenic acids) may be preferably 0.0001, more preferably 0.001.

(v) In the purified chlorogenic acid-containing preparation, the mass ratio [K/chlorogenic acids] of potassium (K) to the chlorogenic acids may be, from the viewpoint of taste and flavor, preferably 0.18 or smaller, more preferably 0.1 or smaller, more preferably 0.08 or smaller, more preferably 0.06 or smaller, even more preferably 0.04 or smaller. It is to be noted that the lower limit of the mass ratio of K/chlorogenic acids is not specifically limited and may be 0. From the viewpoint of production efficiency, the lower limit of the mass ratio of K/chlorogenic acids may be preferably 0.0001, more preferably 0.001, even more preferably 0.003.

On the purified chlorogenic acid-containing preparation according to the present invention, development of broad applications is feasible because it is not only high in clarity but also good in taste and flavor. For example, it is preferred to formulate the purified chlorogenic acid-containing preparation according to the present invention into a food or beverage as it is or after diluting or concentrating the same, more preferably a packaged beverage.

The packaged beverage making use of the purified chlorogenic acid-containing preparation may contain the chlorogenic acids preferably at from 0.05 to 0.9 mass %. From the viewpoint of taste and flavor, its upper limit may be preferably 0.7 mass %, more preferably 0.6 mass %, more preferably 0.5 mass %, even more preferably 0.4 mass %, and on the other hand, its lower limit may be preferably 0.1 mass %, more preferably 0.12 mass %, even more preferably 0.15 mass %.

Concerning the packaged beverage making use of the purified chlorogenic acid-containing preparation, the content mass ratio [(B)/(A)] of the potassium (B) to the chlorogenic acids (A) in the beverage may be preferably 0.18 or smaller, and from the viewpoint of still further improvements in taste and flavor, more preferably 0.1 or smaller, more preferably 0.08 or smaller, more preferably 0.06 or smaller, even more preferably 0.04 or smaller. It is to be noted that the lower limit of the content mass ratio [(B)/(A)] is not specifically limited and may be 0. From the viewpoint of production efficiency, the lower limit of the content mass ratio [(B)/(A)] may be preferably 0.0001, more preferably 0.001, even more preferably 0.003.

Further, the content of potassium in the beverage may be preferably 0.06 mass % or lower, more preferably 0.03 mass % or lower, even more preferably 0.02 mass % or lower. It is to be noted that the lower limit of the content of potassium in the beverage may be preferably 0.00001 mass % from the viewpoint of production efficiency.

The packaged beverage according to the present invention may further contain (C) sodium. The mass ratio [(K+Na)/chlorogenic acids] of the sum of the potassium (B) and sodium (C) to the chlorogenic acids (A) may be, from the viewpoint of taste and flavor, preferably 0.18 or smaller, more preferably 0.14 or smaller, more preferably 0.1 or smaller, even more preferably 0.06 or smaller. It is to be noted that the lower limit of the mass ratio [(K+Na)/chlorogenic acids] is not specifically limited and may be 0. From the viewpoint of production efficiency, the lower limit of the mass ratio of [(K+Na)/chlorogenic acids] may be preferably 0.0001, more preferably 0.001.

The packaged beverage making use of the purified chlorogenic acid-containing preparation according to the present invention may be either a neutral beverage or an acidic beverage. From the viewpoint of taste and flavor, it is preferred to formulate the packaged beverage as an acidic beverage. The pH (20° C.) of the packaged beverage according to the present invention may be, from the viewpoints of stability and taste and flavor, preferably from 1.5 to 4, more preferably from 2 to 4, more preferably from 2.2 to 3.8, more preferably from 2.5 to 3.5, even more preferably from 2.5 to 3.3.

In the packaged beverage making use of the purified chlorogenic acid-containing preparation according to the present invention, one or more of additives may be added as needed. These additives may include a sweetener, a bitterness suppressor, an antioxidant, a flavor, an inorganic salt, a colorant, an emulsifier, a preservative, a seasoning agent, a quality stabilizer or the like. It is to be noted that the content of such additive may be suitably determined in ranges that do not impair the objects of the present invention.

The beverage making use of the purified chlorogenic acid-containing preparation according to the present invention may be provided by filling it in a conventional package such as a molded package made of polyethylene terephthalate as a principal component (a so-called PET bottle), a metal can, a paper package combined with metal foils or plastic films, a bottle or the like.

The beverage making use of the purified chlorogenic acid-containing preparation according to the present invention can be produced, for example, by filling it in a package like a metal can and after that, when heat sterilization is feasible, conducting the heat sterilization under sterilization conditions prescribed in relevant regulations (in Japan, the Food Sanitation Act). For those which cannot be subjected to retort sterilization like PET bottles or paper packages, a process may be adopted such that the beverage is sterilized beforehand at a high temperature for a short time under similar sterilization conditions as those described above, for example, by a plate-type heat exchanger or the like, is cooled to a particular temperature, and is then filled in packages.

EXAMPLES

1. Evaluation of Purified Chlorogenic Acid-Containing Preparations
[Evaluation Method]

The preparations obtained in the respective Examples and Comparative Examples were each diluted with distilled water to a chlorogenic acid concentration of 0.6 mass %, and phosphoric acid or sodium bicarbonate was added as needed to adjust the pH to 3 so that a beverage was prepared. The beverage was provided as "an evaluation solution", the turbidity and taste and flavor of which were evaluated. Evaluation results are shown in Tables 2 and 3.

(1) Evaluation of Turbidity

Using a turbidimeter ("TURBIDIMETER/TN-100", manufactured by Eutech Instruments Pte Ltd.), each "evaluation solution" was measured at 20° C.

(2) Evaluation of Taste and Flavor

Each "evaluation solution" was tasted by a panel of five experts, and with respect to coarseness and harshness, evaluations were made in accordance with the following standards. Subsequently, final scores were determined upon deliberation.

(Evaluation Standards for Coarseness)
    1: Little coarseness
    2: A little coarseness
    3: Some coarseness
    4: Much coarseness (Evaluation Standards for Harshness)
1: Little harshness
2: A little harshness
3: Some harshness
4: Much harshness 2. Measuring Methods for Chlorogenic Acids and Caffeine
(Analyzer)
HPLC (manufactured by Hitachi, Ltd.) was used. The followings are the model numbers of component units in the analyzer.
Pump unit (with a built-in degasser): "L-2130",
Autosampler (equipped with a cooler): "L-2200",
Column oven: "L-2300",
Separation column: "CADENZA CD-C18", size: 4.6 mm i.d.×150 mm, 3 µm (Intact Corp.), and
Detector (UV-visible spectrophotometer): "L-2420".
(Analysis Conditions)
Sample injection volume: 10 µL,
Flow rate: 1.0 mL/min,
Detection wavelength of the UV-visible spectrophotometer: 325 nm (for chlorogenic acids),
270 nm (for caffeine),
Eluent A: 5% acetonitrile containing 0.05 mol/L of acetic acid, 0.01 mol/L of sodium acetate and
0.1 mmol/L of HEDPO, and
Eluent B: acetonitrile.

TABLE 1

| (Concentration gradient conditions) | | |
|---|---|---|
| Time (min) | Eluent A (% (v/v)) | Eluent B (% (v/v)) |
| 0 | 100 | 0 |
| 10 | 100 | 0 |
| 15 | 95 | 5 |
| 20 | 95 | 5 |
| 22 | 92 | 8 |
| 50 | 92 | 8 |
| 52 | 10 | 90 |
| 60 | 10 | 90 |
| 60.1 | 100 | 0 |
| 70 | 100 | 0 |

(Retention time of chlorogenic acids)
3-caffeoylquinic acid (3-CQA): 5.2 min,
5-caffeoylquinic acid (5-CQA): 8.7 min,
4-caffeoylquinic acid (4-CQA): 11.2 min,
3-feruloylquinic acid (3-FQA): 12.6 min,
5-feruloylquinic acid (5-FQA): 19.1 min,
4-feruloylquinic acid (4-FQA): 20.9 min,
3,5-dicaffeoylquinic acid (3,5-diCQA): 37.0 min,
3,4-dicaffeoylquinic acid (3,4-diCQA): 37.5 min, and
4,5-dicaffeoylquinic acid (4,5-diCQA): 44.8 min.

From the area % values determined above, the mass % of the chlorogenic acids was determined by using 5-CQA as a standard substance.
(Retention Time of Caffeine)
18.8 min
From the area % value determined above, the mass % of caffeine was determined by using reagent-grade caffeine as a standard substance.
3. Measuring Methods for Potassium and Sodium
Potassium (K) and sodium (Na) were measured by an atomic absorption photometer ("HITACHI POLARIZED ZEEMAN ATOMIC ABSORPTION PHOTOMETER, MODEL: Z-6100").

Example 1

Green coffee beans of Robusta were extracted with hot water, and the resulting extract solution was spray-dried to obtain a chlorogenic acid-containing composition as a starting material. In the chlorogenic acid-containing composition as the starting material, the content of the chlorogenic acids was 40.8 mass %, the caffeine content was 9.8 mass %, the mass ratio (caffeine content/chlorogenic acids) was 0.241, and the mass ratio ((K+Na)/chlorogenic acids) was 0.19.

The chlorogenic acid-containing composition (189 g) as the starting material was mixed with an aqueous ethanol solution (756 g) having an ethanol concentration of 52.4 mass %, acid clay ("MIZUKA ACE #600", product of Mizusawa Chemical Industries, Ltd.; 94.5 g) and a filter aid ("SOLKA FLOCK", product of Nippon Mining Procurement, Inc.; 10.7 g) to obtain a "chlorogenic acid-containing slurry" (1,051 g). The pH of the "chlorogenic acid-containing slurry" was 5.7. The chlorogenic acid-containing composition as the starting material amounted to 25 mass parts per 100 mass parts of the aqueous ethanol solution. The acid clay was used in an amount of 50 mass parts relative to 100 mass parts of the solids in the chlorogenic acid-containing composition as the starting material.

Next, the "chlorogenic acid-containing slurry" (1,051 g) and an aqueous ethanol solution (189 g) having an ethanol concentration of 52.4 mass % were filtered through No. 2 filter paper with diatomaceous earth deposited as a precoat thereon, and a "filtrate" (1,054 g) was collected.

Through a column packed with activated carbon ("SHIRO-WASHI WH2C", product of Japan EnviroChemicals, Ltd.; 132 mL) and another column packed with a H-type cation exchange resin ("SK1BH", product of Mitsubishi Chemical Corporation; 105 mL), the "filtrate" (1,019 g) and an aqueous ethanol solution (231 g) having an ethanol concentration of 52.4 mass % were then passed in this order to collect a "column-treated solution" (1,072 g).

The activated carbon was used in an amount of 0.81 mass times (g/g) relative to the content of the chlorogenic acids in the chlorogenic acid-containing composition as the starting material. The ion exchange resin was used in an amount of 0.74 (mL/g) relative to the content of the solids in the chlorogenic acid-containing composition as the starting material.

After the "column-treated solution" (1,038 g) was filtered through a 0.2-µm membrane filter, the ethanol was distilled off by a rotary evaporator to obtain a solution (225 g) of chlorogenic acid-containing composition. This solution will hereinafter be called the "solution A of chlorogenic acid-containing composition".

In the "solution A of chlorogenic acid-containing composition", the content of the chlorogenic acids was 22.6 mass %, the content of caffeine was 0.29 mass %, the mass ratio (caffeine/chlorogenic acids) was 0.013, the ethanol concentration was 0 mass %, and the pH was 3.1.

The concentration of the chlorogenic acids in the "solution A of chlorogenic acid-containing composition" was then adjusted to 3 mass % with distilled water to obtain a "concentration-adjusted solution of chlorogenic acid-containing composition". The pH was 3.1.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "purified chlorogenic acid-containing preparation". Using the resultant "purified chlorogenic acid-containing preparation", a beverage was prepared under the conditions of the "evaluation method", and was evaluated. The results are shown in Table 2.

Example 2

By the same procedure as in Example 1, a "solution A of chlorogenic acid-containing composition" was obtained.

The concentration of the chlorogenic acids in the "solution A of chlorogenic acid-containing composition" was then adjusted to 5 mass % with distilled water to obtain a "concentration-adjusted solution of chlorogenic acid-containing composition". The pH was 3.1.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "purified chlorogenic acid-containing preparation". Using the resultant "purified chlorogenic acid-containing preparation", a beverage was prepared under the conditions of the "evaluation method", and was evaluated. The results are shown in Table 2.

Example 3

By the same procedure as in Example 1, a "solution A of chlorogenic acid-containing composition" was obtained.

The concentration of the chlorogenic acids in the "solution A of chlorogenic acid-containing composition" was then adjusted to 6 mass % with distilled water to obtain a "concentration-adjusted solution of chlorogenic acid-containing composition". The pH was 3.1.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "purified chlorogenic acid-containing preparation". Using the resultant "purified chlorogenic acid-containing preparation", a beverage was prepared under the conditions of the "evaluation method", and was evaluated. The results are shown in Table 2.

Example 4

By the same procedure as in Example 1, a "solution A of chlorogenic acid-containing composition" was obtained.

The concentration of the chlorogenic acids in the "solution A of chlorogenic acid-containing composition" was then adjusted to 8 mass % with distilled water to obtain a "concentration-adjusted solution of chlorogenic acid-containing composition". The pH was 3.1.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "purified chlorogenic acid-containing preparation". Using the resultant "purified chlorogenic acid-containing preparation", a beverage was prepared under the conditions of the "evaluation method", and was evaluated. The results are shown in Table 2.

Example 5

By the same procedure as in Example 1 except that in the preparation of the "solution A of chlorogenic acid-containing composition", the pH adjustment through the column packed with the H-type cation exchange resin was not conducted, a solution of chlorogenic acid-containing composition was obtained. This solution will hereinafter be called the "solution B of chlorogenic acid-containing composition".

In the resultant "solution B of chlorogenic acid-containing composition", the content of the chlorogenic acids was 23.4 mass %, the content of caffeine was 0.72 mass %, the mass ratio (caffeine/chlorogenic acids) was 0.032, the ethanol concentration was 0 mass %, and the pH was 5.5.

The concentration of the chlorogenic acids in the "solution B of chlorogenic acid-containing composition" was then adjusted to 6 mass % with distilled water, and to an aliquot (12.1 g) of the solution, phosphoric acid (0.29 g) was added to obtain a "concentration-adjusted solution of chlorogenic acid-containing composition". The pH was 3.1.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "purified chlorogenic acid-containing preparation". Using the resultant "purified chlorogenic acid-containing preparation", a beverage was prepared under the conditions of the "evaluation method", and was evaluated. The results are shown in Table 2.

Example 6

By the same procedure as in Example 1, a "solution A of chlorogenic acid-containing composition" was obtained.

The concentration of the chlorogenic acids in the "solution A of chlorogenic acid-containing composition" was then adjusted to 6 mass % with distilled water, and to an aliquot (12.0 g) of the solution, phosphoric acid (0.12 g) and sodium bicarbonate (0.017 g) were added to obtain a "concentration-adjusted solution of chlorogenic acid-containing composition". The pH was 2.5.

After an aliquot (10 g) of the "concentration-adjusted solution of chlorogenic acid-containing composition" was sampled in a centrifuge tube, centrifugal separation was conducted under conditions of 3,000 rpm, 15° C. and 60 minutes to obtain a "purified chlorogenic acid-containing preparation". Using the resultant "purified chlorogenic acid-containing preparation", a beverage was prepared under the conditions of the "evaluation method", and was evaluated. The results are shown in Table 2.

Example 7

Similar to Example 1 except that in the preparation of the "solution A of chlorogenic acid-containing composition", the chlorogenic acid-containing composition as the starting material was changed to a chlorogenic acid-containing composition extracted from roasted coffee beans having the degree of roast (L value) of which was 35, the procedure up to the distillation of ethanol was conducted to obtain a solution of chlorogenic acid-containing composition. This solution will hereinafter be called the "solution D of chlorogenic acid-containing composition".

In the chlorogenic acid-containing composition used as the starting material, the content of the chlorogenic acids was 12.0 mass %, the content of caffeine was 3.91 mass %, the mass ratio (caffeine/chlorogenic acids) was 0.327, the solids concentration was 37.8 mass %, the mass ratio ((K+Na)/chlorogenic acids) was 0.27, and the pH was 5.8.

The activated carbon was used in an amount 1.08 mass times (g/g) relative to the content of the chlorogenic acids in the chlorogenic acid-containing composition as the starting material. The ion exchange resin was used in an amount of 0.73 (mL/g) relative to the solids content in the chlorogenic acid-containing composition as the starting material.

In the thus-obtained "solution D of chlorogenic acid-containing composition", the content of the chlorogenic acids was 15.9 mass %, the content of caffeine was 0.53 mass %, the mass ratio (caffeine/chlorogenic acids) was 0.034, the ethanol concentration was 0 mass %, and the pH was 3.0. It is to be noted that the pH of the "chlorogenic acid-containing slurry" was 5.8.

The concentration of the chlorogenic acids in the "solution D of chlorogenic acid-containing composition" was then adjusted to 3 mass % with distilled water to obtain a "concentration-adjusted solution of chlorogenic acid-containing composition". The pH was 3.0.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "purified chlorogenic acid-containing preparation". Using the resultant "purified chlorogenic acid-containing preparation", a beverage was prepared under the conditions of the "evaluation method", and was evaluated. The results are shown in Table 2.

Comparative Example 1

Using the "chlorogenic acid-containing composition" employed as the starting material in Example 1, a beverage was prepared under the conditions of the "evaluation method", and was evaluated. The results are shown in Table 2.

Comparative Example 2

Using the "solution A of chlorogenic acid-containing composition", a beverage was prepared under the conditions of the "evaluation method", and was evaluated. The results are shown in Table 2.

Comparative Example 3

By the same procedure as in Example 1 except that in the preparation of the "solution A of chlorogenic acid-containing composition", the acid clay ("MIZUKA ACE #600") was not added upon bringing the "chlorogenic acid-containing composition" into contact with the 52.4 mass % aqueous solution of ethanol, a solution of chlorogenic acid-containing composition was obtained. It is to be noted that the pH of the "chlorogenic acid-containing slurry" was 5.7. This solution will hereinafter be called the "solution C of chlorogenic acid-containing composition".

The activated carbon was used in an amount 0.82 mass times (g/g) relative to the content of the chlorogenic acids in the chlorogenic acid-containing composition as the starting material. The ion exchange resin was used in an amount of 0.66 (mL/g) relative to the solids content of the chlorogenic acid-containing composition as the starting material.

In the thus-obtained "solution C of chlorogenic acid-containing composition", the content of the chlorogenic acids was 17.9 mass %, the content of caffeine was 0.36 mass %, the mass ratio (caffeine/chlorogenic acids) was 0.020, the ethanol concentration was 0 mass %, and the pH was 3.2.

The concentration of the chlorogenic acids in the "solution C of chlorogenic acid-containing composition" was then adjusted to 6 mass % with distilled water to obtain a "concentration-adjusted solution of chlorogenic acid-containing composition". The pH was 3.2.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "chlorogenic acid-containing preparation". Using the resultant "chlorogenic acid-containing preparation", a beverage was prepared under the conditions of the "evaluation method", and was evaluated.

The results are shown in Table 2.

Comparative Example 4

By the same procedure as in Example 1, a "solution A of chlorogenic acid-containing composition" was obtained.

The concentration of the chlorogenic acids in the "solution A of chlorogenic acid-containing composition" was then adjusted to 1 mass % with distilled water to obtain a "concentration-adjusted solution of chlorogenic acid-containing composition". The pH was 3.1.

After an aliquot (10 g) of the "concentration-adjusted solution of chlorogenic acid-containing composition" was sampled in a centrifuge tube, centrifugal separation was conducted under conditions of 3,000 rpm, 15° C. and 60 minutes to obtain a "chlorogenic acid-containing preparation". Using the resultant "chlorogenic acid-containing preparation", a beverage was prepared under the conditions of the "evaluation method", and was evaluated. The results are shown in Table 2.

Comparative Example 5

By the same procedure as in Example 1, a "solution A of chlorogenic acid-containing composition" was obtained.

The concentration of the chlorogenic acids in the "solution A of chlorogenic acid-containing composition" was then adjusted to 11 mass % with distilled water to obtain a "concentration-adjusted solution of chlorogenic acid-containing composition". The pH was 3.1.

After an aliquot (10 g) of the "concentration-adjusted solution of chlorogenic acid-containing composition" was sampled in a centrifuge tube, centrifugal separation was conducted under conditions of 3,000 rpm, 15° C. and 60 minutes to obtain a "chlorogenic acid-containing preparation". Using the resultant "chlorogenic acid-containing preparation", a beverage was prepared under the conditions of the "evaluation method", and was evaluated. The results are shown in Table 2.

Comparative Example 6

By the same procedure as in Example 1, a "solution A of chlorogenic acid-containing composition" was obtained.

After an aliquot (10 g) of the "solution A of chlorogenic acid-containing composition" was sampled in a centrifuge tube without conducting its concentration adjustment, that is, while the concentration of the chlorogenic acids was maintained at 22.6 mass %, centrifugal separation was conducted under conditions of 3,000 rpm, 15° C. and 60 minutes to obtain a "chlorogenic acid-containing preparation". Using the resultant "chlorogenic acid-containing preparation", a beverage was prepared under the conditions of the "evaluation method", and was evaluated. The results are shown in Table 2.

Comparative Example 7

By the same procedure as in Example 1, a "solution A of chlorogenic acid-containing composition" was obtained.

The concentration of the chlorogenic acids in the "solution A of chlorogenic acid-containing composition" was then adjusted to 6 mass % with distilled water, and to an aliquot (12.0 g) of the solution, sodium bicarbonate (0.121 g) was added to obtain a "concentration-adjusted solution of chlorogenic acid-containing composition". The pH was 4.1.

After an aliquot (10 g) of the "concentration-adjusted solution of chlorogenic acid-containing composition" was sampled in a centrifuge tube, centrifugal separation was conducted under conditions of 3,000 rpm, 15° C. and 60 minutes to obtain a "chlorogenic acid-containing preparation". Using the resultant "chlorogenic acid-containing preparation", a beverage was prepared under the conditions of the "evaluation method", and was evaluated. The results are shown in Table 2.

Comparative Example 8

By the same procedure as in Example 1, a "solution A of chlorogenic acid-containing composition" was obtained.

The concentration of the chlorogenic acids in the "solution A of chlorogenic acid-containing composition" was then adjusted to 6 mass % with distilled water, and to an aliquot (12.0 g) of the solution, sodium bicarbonate (0.29 g) was added to obtain a "concentration-adjusted solution of chlorogenic acid-containing composition". The pH was 5.5.

After an aliquot (10 g) of the "concentration-adjusted solution of chlorogenic acid-containing composition" was sampled in a centrifuge tube, centrifugal separation was conducted under conditions of 3,000 rpm, 15° C. and 60 minutes to obtain a "chlorogenic acid-containing preparation". Using the resultant "chlorogenic acid-containing preparation", a beverage was prepared under the conditions of the "evaluation method", and was evaluated. The results are shown in Table 2.

Example 8

Green coffee beans of Robusta were extracted with hot water, and the resulting extract solution was concentrated by a rotary evaporator. Ethanol was added thereto to obtain a chlorogenic acid-containing composition as a starting material. In the chlorogenic acid-containing composition as the starting material, the solids concentration was 59.8 mass %, the content of the chlorogenic acids was 30.8 mass %, the caffeine content was 5.6 mass %, the mass ratio (caffeine content/chlorogenic acids) was 0.183, the mass ratio ((K+Na)/chlorogenic acids) was 0.18, the pH was 5.8, and the ethanol concentration was 4.5 mass %.

The chlorogenic acid-containing composition (151 g) as the starting material was mixed with an aqueous ethanol solution (300 g) having an ethanol concentration of 69.9 mass %, acid clay ("MIZUKA ACE #600", product of Mizusawa Chemical Industries, Ltd.; 45.0 g) and a filter aid ("SOLKA FLOCK", product of Nippon Mining Procurement, Inc.; 5.1 g) to obtain a "chlorogenic acid-containing slurry" (500 g). The pH of the "chlorogenic acid-containing slurry" was 5.7. The chlorogenic acid-containing composition amounted to 25 mass parts relative to 100 mass parts of the aqueous organic solvent solution. The acid clay was used in an amount of 50 mass parts per 100 mass parts of the solids in the chlorogenic acid-containing composition. Also, the concentration of ethanol in the "chlorogenic acid-containing slurry" was 60 mass %.

Next, the "chlorogenic acid-containing slurry" (478 g) and an aqueous ethanol solution (90 g) having an ethanol concentration of 60 mass % were filtered through No. 2 filter paper with diatomaceous earth deposited as a precoat thereon, and a "filtrate" (486 g) was collected.

Through a column packed with activated carbon ("SHIROWASHI WH2C", product of Japan EnviroChemicals, Ltd.; 34 mL) and anther column packed with a H-type cation exchange resin ("SK1BH", product of Mitsubishi Chemical Corporation; 31 mL), the "filtrate" (464 g) and an aqueous organic solvent solution (116 g) having an ethanol concentration of 60 mass % were then passed to collect a "column-treated solution" (481 g).

The activated carbon was used in an amount 0.70 mass times (g/g) relative to the content of the chlorogenic acids in the chlorogenic acid-containing composition as the starting material. The ion exchange resin was used in an amount of 0.85 (mL/g) relative to the solids content in the chlorogenic acid-containing composition as the starting material.

After the "column-treated solution" (464 g) was filtered through a 0.2-μm membrane filter, the ethanol was distilled off by a rotary evaporator to obtain a solution (118 g) of chlorogenic acid-containing composition. This solution will hereinafter be called the "solution E of chlorogenic acid-containing composition".

In the "solution E of chlorogenic acid-containing composition", the content of the chlorogenic acids was 26.3 mass %, the content of caffeine was 0.34 mass %, the ratio of caffeine/chlorogenic acids was 0.013, the ethanol concentration was 0 mass %, and the pH was 2.0.

The concentration of the chlorogenic acids in the "solution E of chlorogenic acid-containing composition" was then adjusted to 6 mass % with distilled water to obtain a "concentration-adjusted solution of chlorogenic acid-containing composition". The pH was 2.0.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "purified chlorogenic acid-containing preparation". Using the resultant "purified chlorogenic acid-containing preparation", a beverage was prepared under the conditions of the "evaluation method", and was evaluated. The results are shown in Table 3.

Example 9

By the same procedure as in Example 8 except that in the preparation of the "solution E of chlorogenic acid-containing composition" of Example 8, the packed amount of the cation exchange resin ("SK1BH", product of Mitsubishi Chemical Corporation) was changed to 24 mL, a solution of chlorogenic acid-containing composition was obtained. This solution will hereinafter be called the "solution F of chlorogenic acid-containing composition".

The activated carbon was used in an amount 0.70 mass times (g/g) relative to the content of the chlorogenic acids in the chlorogenic acid-containing composition as the starting material. The ion exchange resin was used in an amount of 0.64 (mL/g) relative to the solids content of the chlorogenic acid-containing composition as the starting material.

In the thus-obtained "solution F of chlorogenic acid-containing composition", the content of the chlorogenic acids was 26.3 mass %, the content of caffeine was 0.34 mass %, the mass ratio (caffeine/chlorogenic acids) was 0.013, the ethanol concentration was 0 mass %, and the pH was 2.8.

The concentration of the chlorogenic acids in the "solution F of chlorogenic acid-containing composition" was then adjusted to 6 mass % with distilled water to obtain a "concentration-adjusted solution of chlorogenic acid-containing composition". The pH was 2.8.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "chlorogenic acid-containing preparation". Using the resultant "purified chlorogenic acid-containing preparation", a beverage was prepared under the conditions of the "evaluation method", and was evaluated. The results are shown in Table 3.

Example 10

By the same procedure as in Example 8 except that in the preparation of the "solution E of chlorogenic acid-containing composition" of Example 8, the packed amount of the H-type cation exchange resin ("SK1BH", product of Mitsubishi Chemical Corporation) was changed to 16 mL, a solution of chlorogenic acid-containing composition was obtained. This solution will hereinafter be called the "solution G of chlorogenic acid-containing composition".

The activated carbon was used in an amount 0.70 mass times (g/g) relative to the content of the chlorogenic acids in the chlorogenic acid-containing composition as the starting material. The ion exchange resin was used in an amount of 0.42 (mL/g) relative to the solids content of the chlorogenic acid-containing composition as the starting material.

In the thus-obtained "solution G of chlorogenic acid-containing composition", the content of the chlorogenic acids was 26.3 mass %, the content of caffeine was 0.34 mass %, the mass ratio (caffeine/chlorogenic acids) was 0.013, the ethanol concentration was 0 mass %, and the pH was 3.4.

The concentration of the chlorogenic acids in the "solution G of chlorogenic acid-containing composition" was then adjusted to 6 mass % with distilled water to obtain a "concentration-adjusted solution of chlorogenic acid-containing composition". The pH was 3.4.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "chlorogenic acid-containing preparation". Using the resultant "purified chlorogenic acid-containing preparation", a beverage was prepared under the conditions of the "evaluation method", and was evaluated. The results are shown in Table 3.

Example 11

By the same procedure as in Example 10 except that in the preparation of the "solution G of chlorogenic acid-containing composition" of Example 10, the chlorogenic acid-containing composition as the starting material was changed, a solution of chlorogenic acid-containing composition was obtained. This solution will hereinafter be called the "solution H of chlorogenic acid-containing composition".

The activated carbon was used in an amount 0.86 mass times (g/g) relative to the content of the chlorogenic acids in the chlorogenic acid-containing composition as the starting material. The ion exchange resin was used in an amount of 0.53 (mL/g) relative to the solids content in the chlorogenic acid-containing composition as the starting material.

In the chlorogenic acid-containing composition used as the starting material, the solids concentration was 100 mass %, the content of the chlorogenic acids was 38.2 mass %, the content of caffeine was 8.5 mass %, the mass ratio (caffeine content/chlorogenic acids) was 0.22, and the mass ratio ((K+Na)/chlorogenic acids) was 0.20.

In the thus-obtained "solution H of chlorogenic acid-containing composition", the content of the chlorogenic acids was 21.6 mass %, the content of caffeine was 0.21 mass %, the mass ratio (caffeine/chlorogenic acids) was 0.010, the ethanol concentration was 0 mass %, and the pH was 3.4.

The concentration of the chlorogenic acids in the "solution H of chlorogenic acid-containing composition" was then adjusted to 6 mass % with distilled water to obtain a "concentration-adjusted solution of chlorogenic acid-containing composition". The pH was 3.4.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "chlorogenic acid-containing preparation". Using the resultant "purified chlorogenic acid-containing preparation", a beverage was prepared under the conditions of the "evaluation method", and was evaluated. The results are shown in Table 3.

Comparative Example 9

By the same procedure as in Example 8 except that in the preparation of the "solution E of chlorogenic acid-containing composition" of Example 8, the H-type cation exchange resin ("SK1BH", product of Mitsubishi Chemical Corporation) was not used, a solution of chlorogenic acid-containing composition was obtained. This solution will hereinafter be called the "solution I of chlorogenic acid-containing composition".

In the thus-obtained "solution I of chlorogenic acid-containing composition", the content of the chlorogenic acids was 26.3 mass %, the content of caffeine was 0.34 mass %, the mass ratio (caffeine/chlorogenic acids) was 0.013, the ethanol concentration was 0 mass %, and the pH was 5.3.

The concentration of the chlorogenic acids in the "solution I of chlorogenic acid-containing composition" was then adjusted to 6 mass % with distilled water to obtain a "concentration-adjusted solution of chlorogenic acid-containing composition". The pH was 5.3.

After an aliquot (10 g) of the thus-obtained "concentration-adjusted solution of chlorogenic acid-containing composition" was sampled in a centrifuge tube, centrifugal separation was conducted under conditions of 3,000 rpm, 15° C. and 60 minutes to obtain a "chlorogenic acid-containing preparation". Using the resultant "chlorogenic acid-containing preparation", a beverage was prepared under the conditions of the "evaluation method", and was evaluated. The results are shown in Table 3.

TABLE 2

| Steps | | Examples | | | | | | |
|---|---|---|---|---|---|---|---|---|
| | | 1 | 2 | 3 | 4 | 5 | 6 | 7 |
| | | Kind of coffee beans as starting material | | | | | | |
| | | Green beans | Green beans | Green beans | Green beans | Green beans | Green beans | Roasted beans |
| 1st | Conc. of organic solvent in aqueous organic solvent solution used for the dispersion or dissolution of chlorogenic acid-containing composition (mass %) | 52.4 | 52.4 | 52.4 | 52.4 | 52.4 | 52.4 | 52.4 |
| | Clay treatment | Treated | Treated | Treated | Treated | Treated | Treated | Treated |
| 2nd | Removal of deposit | Filt. | Filt. | Filt. | Filt. | Filt. | Filt. | Filt. |
| 3rd | Conc. of chlorogenic acids in "solution of chlorogenic acid-containing composition" before concentration adjustment (mass %) | 22.6 | 22.6 | 22.6 | 22.6 | 23.4 | 22.6 | 15.9 |
| | pH adjustment 1 | CA | CA | CA | CA | — | CA | CA |
| | Designation of "solution of chlorogenic acid-containing composition" | A | A | A | A | B | A | D |
| | pH adjustment 2 | — | — | — | — | H3PO4 | H3PO4 NaHCO3 | — |
| | pH (20° C.) | 3.1 | 3.1 | 3.1 | 3.1 | 2.5 | 3.1 | 3.0 |
| | Conc. of chlorogenic acids in "concentration-adjusted solution of chlorogenic acid-containing composition" (mass %) | 3 | 5 | 6 | 8 | 6 | 6 | 6 |
| 4th | Separation of turbidity | CS | CS | CS | CS | CS | CS | CS |
| Analysis* | (K + Na)/chlorogenic acids (mass ratio) | 0.05 | 0.05 | 0.05 | 0.05 | 0.18 | 0.05 | 0.03 |
| | K/chlorogenic acids (mass ratio) | 0.04 | 0.04 | 0.04 | 0.04 | 0.18 | 0.04 | 0.02 |
| Evaluation | Turbidity (NTU) | 40 | 7 | 3 | 13 | 1 | 2 | 45 |
| | Taste and flavor (coarseness) | 1 | 1 | 1 | 1 | 1 | 1 | 1 |
| | Taste and flavor (harshness) | 1 | 1 | 1 | 1 | 4 | 2 | 1 |

| Steps | | Comparative Examples | | | | | | | |
|---|---|---|---|---|---|---|---|---|---|
| | | 1 | 2 | 3 | 4 | 5 | 6 | 7 | 8 |
| | | Kind of coffee beans as starting material | | | | | | | |
| | | Green beans | Green beans | Green beans | Green beans | Green beans | Green beans | Green beans | Green beans |
| 1st | Conc. of organic solvent in aqueous organic solvent solution used for the dispersion or dissolution of chlorogenic acid-containing composition (mass %) | — | 52.4 | 52.4 | 52.4 | 52.4 | 52.4 | 52.4 | 52.4 |
| | Clay treatment | None | Treated | None | Treated | Treated | Treated | Treated | Treated |
| 2nd | Removal of deposit | — | Filt. | Filt. | Filt. | Filt. | Filt. | Filt. | Filt. |
| 3rd | Conc. of chlorogenic acids in "solution of chlorogenic acid-containing composition" before concentration adjustment (mass %) | — | 22.6 | 17.9 | 22.6 | 22.6 | 22.6 | 22.6 | 22.6 |
| | pH adjustment 1 | — | CA | CA | CA | CA | CA | CA | CA |
| | Designation of "solution of chlorogenic acid-containing composition" | — | A | C | A | A | A | A | A |
| | pH adjustment 2 | — | — | — | — | — | — | NaHCO3 | NaHCO3 |
| | pH (20° C.) | — | 3.1 | 3.2 | 3.1 | 3.1 | 3.1 | 4.1 | 5.5 |
| | Conc. of chlorogenic acids in "concentration-adjusted solution of chlorogenic acid-containing composition" (mass %) | — | 22 | 6 | 1 | 11 | 22 | 6 | 6 |
| 4th | Separation of turbidity | — | None | CS | CS | CS | CS | CS | CS |
| Analysis* | (K + Na)/chlorogenic acids (mass ratio) | 0.19 | 0.05 | 0.05 | 0.05 | 0.05 | 0.05 | 0.06 | 0.08 |
| | K/chlorogenic acids (mass ratio) | 0.19 | 0.04 | 0.04 | 0.04 | 0.04 | 0.04 | 0.04 | 0.06 |

TABLE 2-continued

| Evaluation | Turbidity (NTU) | 500< | 500< | 66 | 75 | 239 | 500< | 400 | 500< |
|---|---|---|---|---|---|---|---|---|---|
| | Taste and flavor (coarseness) | 4 | 4 | 2 | 2 | 2 | 4 | 3 | 4 |
| | Taste and flavor (harshness) | 4 | 1 | 1 | 1 | 1 | 1 | 2 | 2 |

CA: cation exchange resin, "SK1BH" (product of Mitsubishi Chemical Corporation)
CS: centrifugal separation
*Analysis data of purified chlorogenic acid preparations

TABLE 3

| | | Examples | | | | Comp. Ex. |
|---|---|---|---|---|---|---|
| | | 8 | 9 | 10 | 11 | 9 |
| | | Kind of Coffee Beans as Starting material | | | | |
| Steps | | Green beans | Green beans | Green beans | Green beans | Green beans |
| 1st | Conc. of organic solvent in aqueous organic solvent solution used for the dispersion or dissolution of chlorogenic acid-containing composition (mass %) | 60 | 60 | 60 | 60 | 60 |
| | Clay treatment | Treated | Treated | Treated | Treated | Treated |
| 2nd | Removal of deposit | Filt. | Filt. | Filt. | Filt. | Filt. |
| 3rd | Conc. of chlorogenic acids in "solution of chlorogenic acid-containing composition" before concentration adjustment (mass %) | 24.1 | 24.1 | 24.1 | 24.1 | 24.1 |
| | pH adjustment 1 | CA | CA | CA | CA | None |
| | Designation of "solution of chlorogenic acid-containing composition" | E | F | G | H | I |
| | pH adjustment 2 | — | — | — | — | — |
| | pH (20° C.) | 2.0 | 2.8 | 3.4 | 3.4 | 5.3 |
| | Conc. of chlorogenic acids in "concentration-adjusted solution of chlorogenic acid-containing composition" (mass %) | 6 | 6 | 6 | 6 | 6 |
| 4th | Separation of turbidity | CS | CS | CS | CS | CS |
| Analysis* | (K + Na)/chlorogenic acids (mass ratio) | 0.01 | 0.04 | 0.08 | 0.13 | 0.15 |
| | K/chlorogenic acids (mass ratio) | 0.01 | 0.03 | 0.06 | 0.13 | 0.13 |
| Evaluation | Turbidity (NTU) | 25 | 1 | 1 | 10 | 500> |
| | Taste and flavor (coarseness) | 1 | 1 | 1 | 1 | 4 |
| | Taste and flavor (harshness) | 1 | 1 | 2 | 3 | 4 |

CA: cation exchange resin, "SK1BH" (product of Mitsubishi Chemical Corporation)
CS: centrifugal separation
*Analysis data of purified chlorogenic acid preparations It has been confirmed from Tables 2 and 3 that by including as essential requirements the first to fourth steps according to the present invention, a beverage making use of the resulting purified chlorogenic acid-containing preparation is reduced in the occurrence of turbidity even in the acidic range and is also reduced in coarseness.

It has also been confirmed that by adjusting the sum of potassium (K) and sodium (Na) relative to the amount of the chlorogenic acids or the amount of potassium (K) relative to the amount of the chlorogenic acids, harshness can be suppressed, in addition to a reduction in the occurrence of turbidity and a reduction in coarseness.

Example 12

The "purified chlorogenic acid-containing preparation F" obtained in Example 9 was concentrated at 60° C. by a rotary evaporator until the concentration of the chlorogenic acids increased to 15 mass %, whereby a "concentrated, purified chlorogenic acid-containing preparation F1" was obtained.

The "concentrated, purified chlorogenic acid-containing preparation F1" was frozen at −20° C., and subsequently, was thawed. Neither turbidity nor precipitates were observed in the solution, and good clarity was maintained.

Example 13

The "purified chlorogenic acid-containing preparation F" obtained in Example 9 was concentrated at 60° C. by a rotary evaporator until the concentration of the chlorogenic acids increased to 22 mass %, whereby a "concentrated, purified chlorogenic acid-containing preparation F2" was obtained.

The "concentrated, purified chlorogenic acid-containing preparation F2" was frozen at −20° C., and subsequently, was thawed. Neither turbidity nor precipitates were observed in the solution, and good clarity was maintained.

Example 14

The "purified chlorogenic acid-containing preparation F" obtained in Example 9 was concentrated at 60° C. by a rotary evaporator until the concentration of the chlorogenic acids increased to 26 mass %, whereby a "concentrated, purified chlorogenic acid-containing preparation F3" was obtained.

The "concentrated, purified chlorogenic acid-containing preparation F3" was frozen at −20° C., and subsequently, was thawed. Neither turbidity nor precipitates were observed in the solution, and good clarity was maintained.

The invention claimed is:

1. A process for producing a purified chlorogenic acid-containing preparation, comprising:
dispersing or dissolving a chlorogenic acid-containing composition as a starting material in the presence of acid clay or activated clay in a mixed solvent of 10 to 95% of ethanol and water to form a dispersion or solution;
removing a deposit from the dispersion or solution to obtain a first solution;
concentrating the level of chlorogenic acids in the first solution and adjusting the pH of the first solution to a concentration of from 2.5 to 8 mass % and a pH of 2 to 3.5, respectively, to form a concentrated pH-adjusted solution; and
separating a deposit from the concentrated pH-adjusted solution; and
wherein said process further comprises
(i) reducing the concentration of the ethanol in the first solution to 5 mass % or lower; and/or
(ii) reducing the concentration of the ethanol in the concentrated pH-adjusted solution to 5 mass % or lower.

2. The process according to claim 1, wherein said dispersing or dissolving further comprises adjusting a pH of the dispersion or solution, which has been obtained from said dispersing or dissolving, to from 4.6 to 7.

3. The process according to claim 1, wherein the pH adjustment in said adjusting is conducted by at least one method selected from the group consisting of a method that adds an acid to the solution with the chlorogenic acids contained therein, a method that dissolves in an acidic aqueous solution the solution with the chlorogenic acids contained therein, and a method that brings the solution with the chlorogenic acids contained therein into contact with a cation exchange resin.

4. The process according to claim 3, wherein the pH adjustment in said adjusting is conducted by the method that brings the solution with the chlorogenic acids present therein into contact with the cation exchange resin.

5. The process according to claim 1, wherein the chlorogenic acid-containing composition as the starting material comprises a content of chlorogenic acids of from 20 to 70 mass % based on the amount of total solids in the chlorogenic acid-containing composition as the starting material.

6. The process according to claim 2, wherein the pH adjustment in said adjusting is conducted by at least one method selected from the group consisting of a method that adds an acid to the solution with the chlorogenic acids contained therein, a method that dissolves in an acidic aqueous solution the solution with the chlorogenic acids contained therein, and a method that brings the solution with the chlorogenic acids contained therein into contact with a cation exchange resin.

7. The process according to claim 6, wherein the pH adjustment in said adjusting is conducted by the method that brings the solution with the chlorogenic acids present therein into contact with the cation exchange resin.

8. The process according to claim 2, wherein the chlorogenic acid-containing composition as the starting material comprises a content of chlorogenic acids of from 20 to 70 mass % based on the amount of total solids in the chlorogenic acid-containing composition as the starting material.

9. The process according to claim 1, wherein said process comprises reducing the concentration of the ethanol in the first solution to 5 mass % or lower.

10. The process according to claim 1, wherein said process comprises reducing the concentration of the ethanol in the concentrated pH-adjusted solution to 5 mass % or lower.

11. The process according to claim 1, wherein said process comprises:
(i) reducing the concentration of the ethanol in the first solution to 5 mass % or lower; and
(ii) reducing the concentration of the ethanol in the concentrated pH-adjusted solution to 5 mass % or lower.

12. The process according to claim 1, wherein said reducing the concentration of ethanol is by distillation under reduced pressure or normal pressure, extraction, membrane separation or the like, as well as to lower the concentration of the organic solvent by adding water thereto.

* * * * *